United States Patent [19]
Mackool

[11] Patent Number: 5,354,265
[45] Date of Patent: Oct. 11, 1994

[54] FLUID INFUSION SLEEVE

[76] Inventor: Richard J. Mackool, 31-27 41st St., Astoria, N.Y. 11103

[21] Appl. No.: 148,521

[22] Filed: Nov. 15, 1993

Related U.S. Application Data

[63] Continuation-in-part of Ser. No. 998,442, Dec. 30, 1992, Pat. No. 5,286,256.

[51] Int. Cl.$^5$ ............................................. A61B 17/20
[52] U.S. Cl. ............................................. 604/22; 601/2
[58] Field of Search .................. 604/22, 164–171, 604/282; 128/24 AA; 601/2

[56] References Cited

U.S. PATENT DOCUMENTS

| | | | |
|---|---|---|---|
| 4,515,583 | 5/1985 | Sorich | 604/22 |
| 4,681,561 | 7/1987 | Hood et al. | 604/22 |
| 4,808,154 | 2/1989 | Freeman | 604/22 |
| 4,816,018 | 3/1989 | Parisi | 604/22 |
| 5,084,009 | 1/1992 | Mackool | 604/22 |
| 5,123,903 | 6/1992 | Quaid et al. | 604/22 |
| 5,163,433 | 11/1992 | Kagawa et al. | 604/22 |
| 5,211,625 | 5/1993 | Sakurai et al. | 604/22 |
| 5,282,786 | 1/1994 | Ureche | 604/22 |

*Primary Examiner*—C. Fred Rosenbaum
*Assistant Examiner*—Michael Rafa
*Attorney, Agent, or Firm*—Cobrin Gittes & Samuel

[57] ABSTRACT

A surgical instrument for removing a cataract from a patient's eye including a hollow vibrating needle surrounded by two hollow infusion sleeves. The outer sleeve conforms to the incision in the eye and the inner sleeve prevents the outer sleeve from collapsing onto the hollow, vibrating needle.

5 Claims, 5 Drawing Sheets

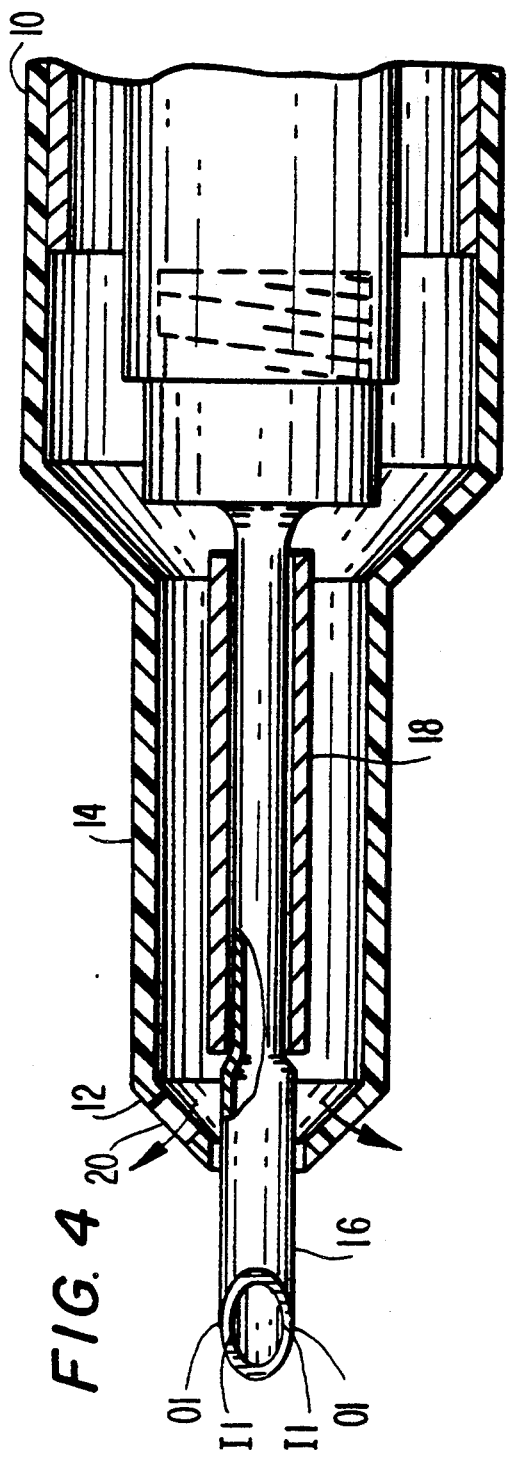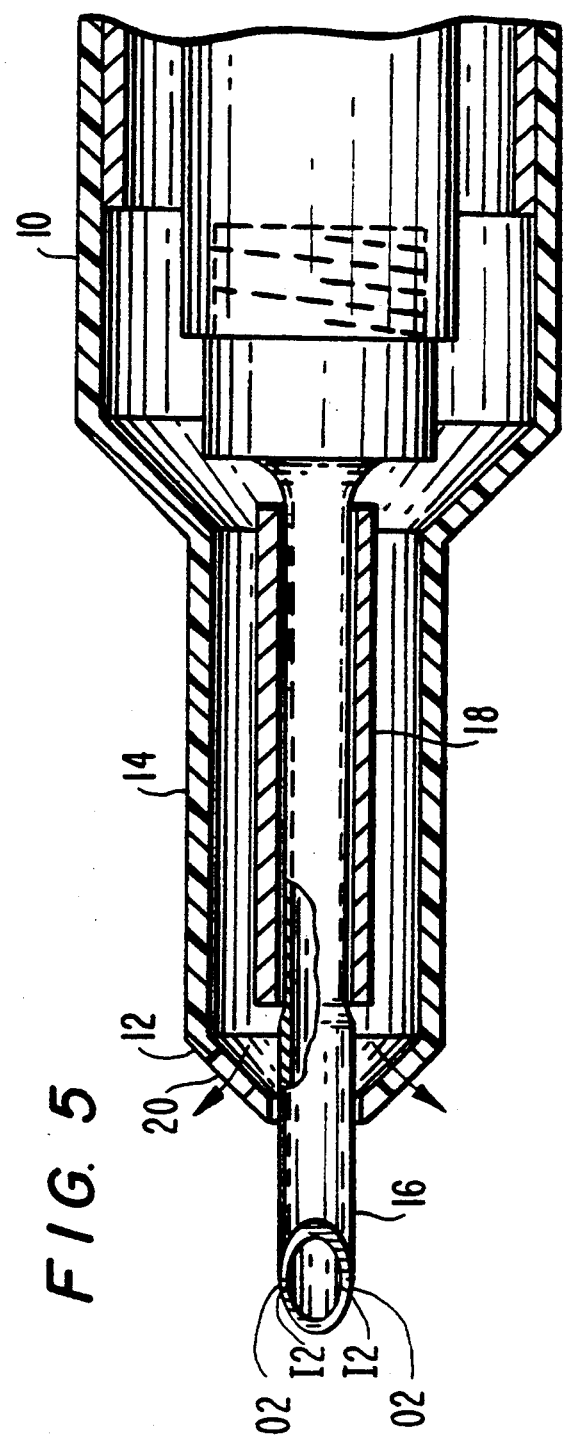

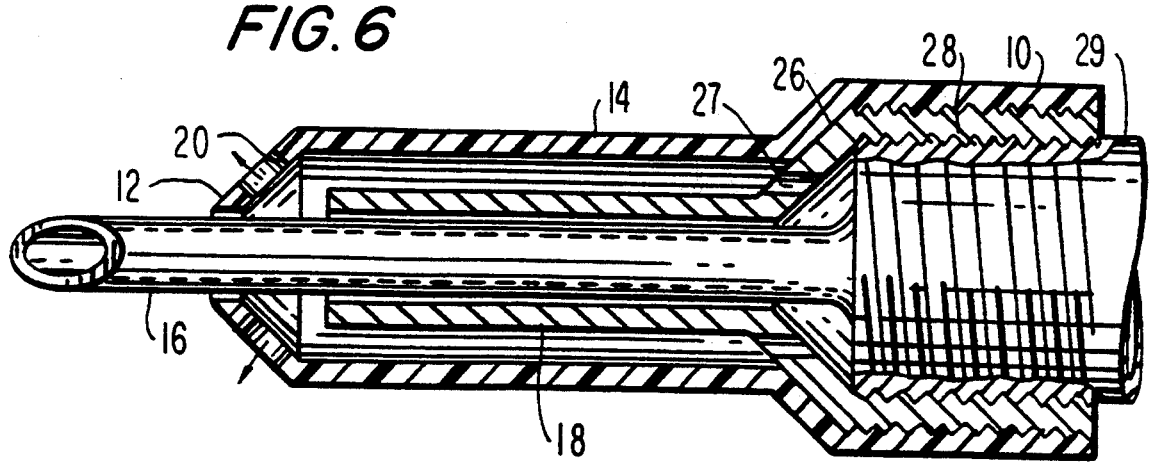
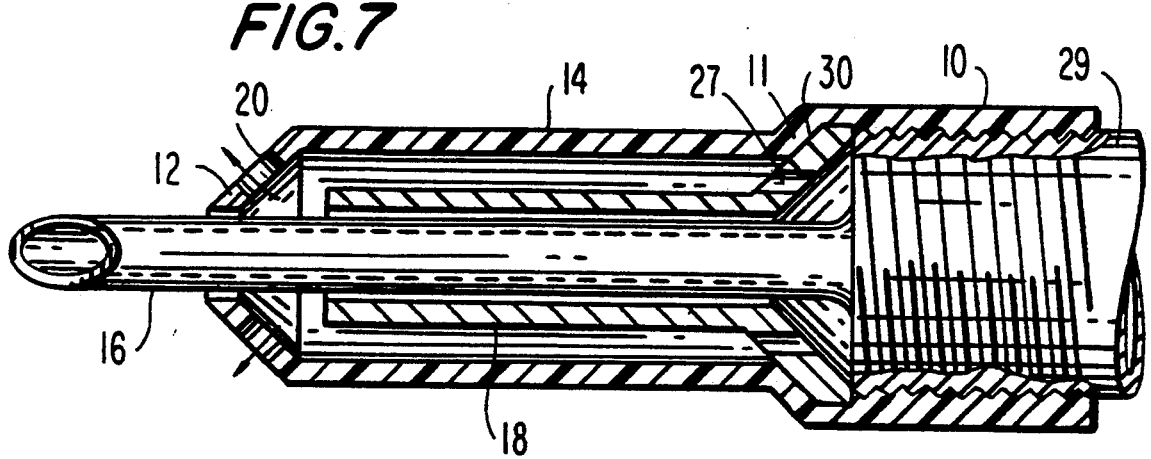
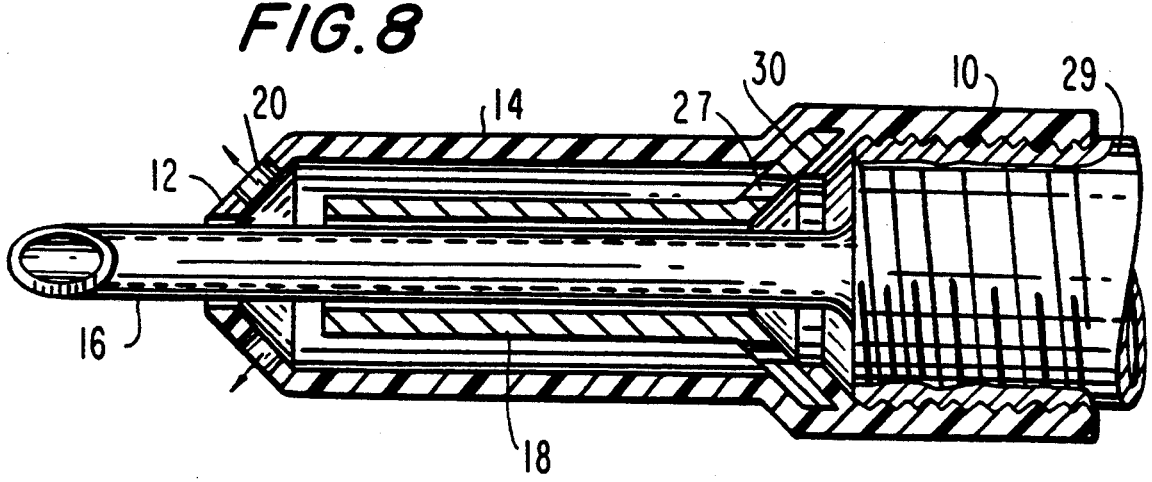

FLUID INFUSION SLEEVE

CROSS REFERENCE TO RELATED APPLICATIONS

This application is a continuation-in-part of my earlier copending application Ser. No. 07/998442 filed 30 Dec. 1992 entitled IMPROVED FLUID INFUSION SLEEVE now U.S. Pat. No. 5,286,256.

BACKGROUND OF THE INVENTION

This invention relates generally to a surgical instrument for use in eye surgery, and, more particularly, relates to a surgical instrument for cataract eye surgery.

A wide array of fluid-irrigated, ultrasonically-operated cutting devices have been developed for ophthalmological surgical techniques such as phacoemulsification—a method for removing a cataract through a surgical incision in the eye. Examples of such devices are set forth in the following patents:

| Patent No. | Inventor |
|---|---|
| 3,589,363 | Banko et al. |
| 4,515,583 | Sorich |
| 4,808,154 | Freeman |
| 4,816,017 | Hood et al. |
| 4,816,018 | Parisi |

U.S. Pat. No. 3,589,363 to Banko et al. and U.S. Pat. No. 4,515,583 to Sorich disclose ultrasonic surgical instruments that utilize rigid outer sleeves.

U.S. Pat. No. 4,808,154 to Freeman discloses a phacoemulsification/irrigation and aspiration sleeve apparatus.

U.S. Pat. No. 4,816,017 to Hood et al. discloses an ultrasonic decoupling sleeve.

U.S. Pat. No. 4,816,018 to Parisi discloses an ultrasonic probe tip.

Fluid-irrigated, ultrasonically-operated cutting devices typical of the prior art, however, suffer from a number of deficiencies. In particular, most infusion sleeves used during phacoemulsification are made of silicone or a silicone-type material. The use of this type of infusion sleeve can cause fluid leakage between the incision edge in the eye and the exterior surface of the infusion sleeve, resulting from a need to make the incision in the eye larger than the infusion sleeve. This need is due to the compressibility of silicone or like materials which cannot be safely used when inserted through an incision in the eye where there is a minimal amount of clearance between the incision and the exterior of the silicone infusion sleeve.

When there is a minimal clearance between the exterior of the silicone infusion sleeve and the incision of the eye, the incision tends to compress the non-rigid silicone infusion sleeve against the vibrating tip which results in relative rubbing movement between the silicone sleeve and the vibrating tip. This relative movement generates undesirable heat as the needle is being vibrated at its relative high frequencies. The generation of this heat is extremely undesirable inasmuch as it can result in thermal burns and shrinkage of the ocular tissue surrounding the silicone infusion sleeve. The burning and shrinkage of ocular tissue is a serious problem with sight-threatening implications.

In an attempt to reduce the infusion fluid leakage and the deleterious effects that can be caused by undesirable friction generated therefrom, some infusion sleeves have been constructed from rigid, non-compressible materials. Generally these materials have consisted of Teflon or metallic-based compositions. These rigid, infusion sleeves have been relatively successful in solving the problems of constriction of the path for fluid flow between the distal end of the infusion sleeve and the vibrating tip as well as the heat generation and thermal burns associated with malleable infusion sleeves; however, other problems persist with these non-compressible infusion sleeves.

While rigid sleeves are capable of being inserted through smaller incisions, which has the advantage of reducing leakage, there is still significant leakage. The primary cause of the persistent leakage between the rigid infusion sleeve and the eye incision is that the cross section of the rigid sleeve does not match the contour of the eye incision. As a consequence, there are fairly substantial gaps between the rigid sleeve exterior surface and the eye incision. This is because the collagen fiber structure of the cornea resists deformity and thus does not readily assume the shape of the infusion sleeve.

The experience of the applicant, who has performed literally thousands of cataract eye operations, has shown that it is impossible, from a practical standpoint, to fully eliminate the problem of leakage during cataract surgery by means of a smaller incision and forcing the rigid infusion sleeve through it. While this may decrease wound leakage, it does not eliminate the problem and it causes the instrument to be so tightly held by the deformed incision that there is great difficulty in advancing and withdrawing the instrument through the incision. As will be apparent to those skilled in the art, during cataract surgery the instrument must be advanced and withdrawn many times through the incision as the fractured portions of the cataract are removed from the various locations within the anterior and posterior chambers of the eye.

Although there are means to prevent leakage, these means are very expensive to construct. They require precision tools with very precise configurations. The invention disclosed in U.S. Pat. No. 5,084,009 to Mackool, addresses the aforementioned problems; however, it also requires concentricity between the rigid infusion sleeve and the vibrating needle.

Accordingly, there exists a need for an improved apparatus for performing cataract surgery.

It is accordingly an object of the invention to provide an improved apparatus for performing cataract surgery.

It is another object of the invention to provide such apparatus that is relatively inexpensive to construct.

Other general and specific objects of the invention will in part be obvious and will in part appear hereinafter.

SUMMARY OF THE INVENTION

The foregoing objects are attained by the invention, which provides a surgical instrument for performing cataract surgery. The instrument includes an outer compressible infusion sleeve having a tapered, ported, distal end, a vibrating needle, and a rigid sleeve surrounding the vibrating needle which prevents the outer compressible sleeve from collapsing against the vibrating needle.

The invention will next be described in connection with certain illustrated embodiments; however, it should be clear to those skilled in the art that various modifications, additions and subtractions can be made without departing from the spirit or scope of the claims.

BRIEF DESCRIPTION OF THE DRAWINGS

For a fuller understanding of the nature and objects of the invention, reference should be made to the following detailed description and the accompanying drawings, in which:

FIG. 4 depicts a third embodiment of a phacoemulsification instrument in accordance with the invention; including details of a rigid, hollow sleeve along with details of a tapered vibrating needle, wherein the inner and outer diameters of the vibrating needles are varied along the length thereof;

FIG. 5 depicts a fourth embodiment of a phacoemulsification instrument in accordance with the invention; including details of a rigid, hollow sleeve along with details of a tapered vibrating needle, wherein the inner diameter of the vibrating needle remains constant and the outer diameter of the vibrating needle changes along the length thereof;

FIG. 6 depicts a fifth embodiment of a phacoemulsification instrument in accordance with the invention; including details of a rigid, hollow sleeve, wherein the rigid hollow sleeve has a ported proximal expansion portion and a threaded extension;

FIG. 7 depicts a sixth embodiment of a phacoemulsification instrument in accordance with the invention; including details of a rigid, hollow sleeve, wherein the rigid hollow sleeve has a ported proximal flange portion;

FIG. 8 depicts a seventh embodiment of a phacoemulsification instrument in accordance with the invention; including details of a rigid, hollow sleeve, wherein the rigid hollow sleeve has a ported proximal flange portion coupled to the deformable sleeve;

DESCRIPTION OF ILLUSTRATED EMBODIMENTS

Figure 1:
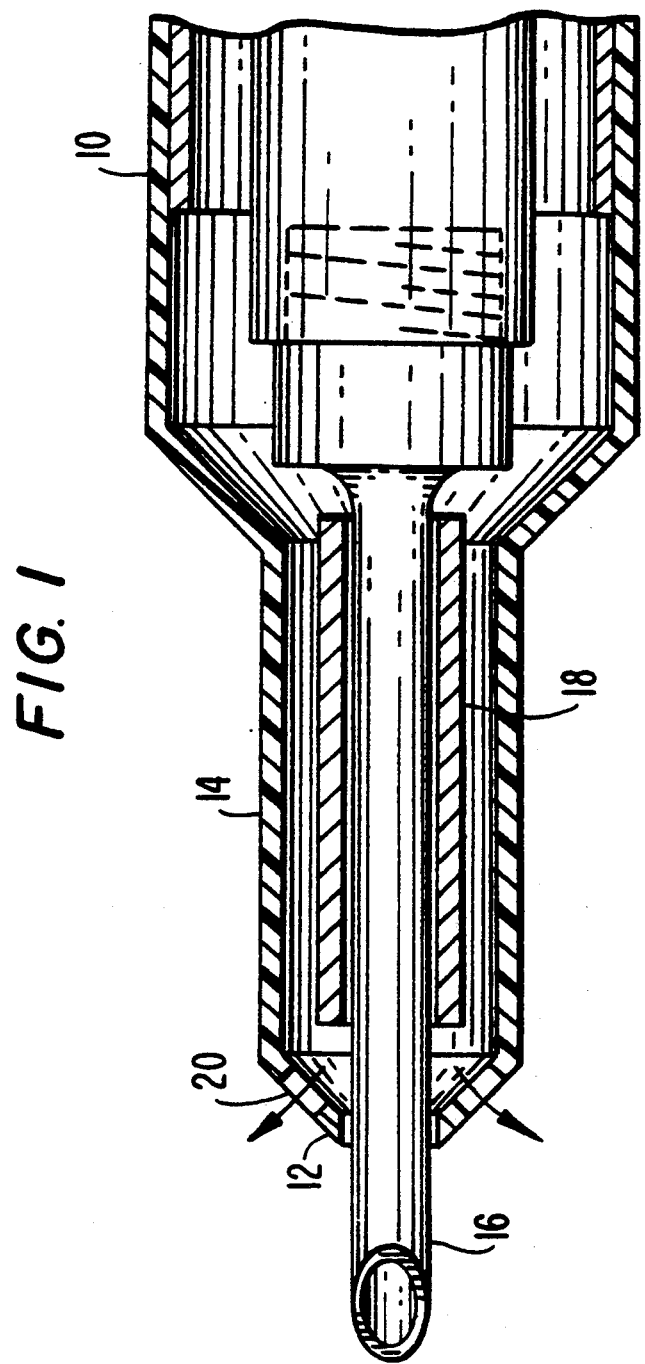
FIG. 1 depicts a cross sectional view of a phacoemulsification instrument modified in accordance with the invention.

FIGS. 1-8 are cross-sectional views of a phacoemulsification instrument including a hollow, compressible infusion sleeve 10 having a tapered, ported, distal end portion 12 and a cylindrical portion 14. The instrument also includes a hollow vibrating needle 16, a rigid, hollow sleeve 18 housing a sleeve body, and discharge ports 20.

Figure 9:
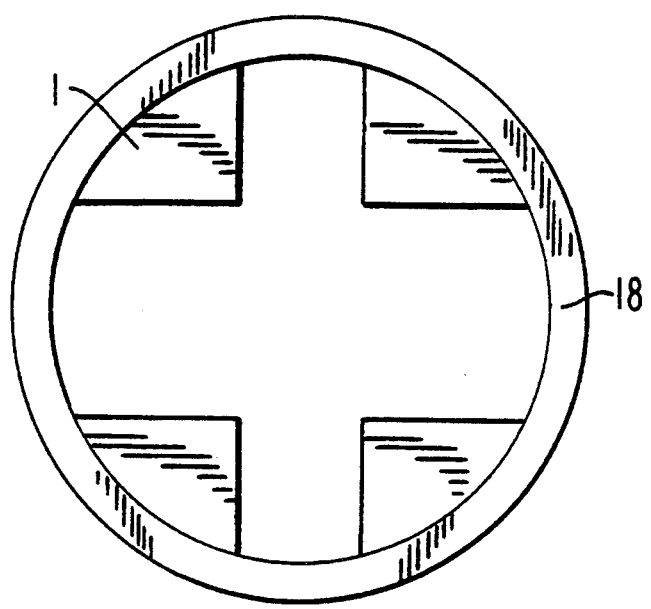
FIG. 9 depicts an embodiment of a rigid hollow sleeve in accordance with the invention for a phacoemulsification instrument.

FIG. 9 is a side view of a rigid, hollow sleeve 18 of a phacoemulsification instrument including spacers 1.

In accordance with known principles of operation employed in phacoemulsification devices, the hollow needle 16 is caused to vibrate at ultrasonic frequencies, causing disintegration of tissue proximate to the tip of needle 16. A saline solution is utilized as a cooling and irrigation fluid, and is introduced at a proximal end of the device and exits through ports 20 located at the tapered, ported distal end 12. Operation of a device of this general nature is described in U.S. Pat. No. 5,084,009 to Mackool, the teachings of which are incorporated by reference herein.

In conventional phacoemulsification devices utilizing a flexible infusion sleeve, the flexible infusion sleeve can collapse around the vibrating needle, causing heat build-up due to friction between the sleeve and the needle. The invention obviates this problem by utilizing inner sleeve 18. In particular, the rigid, hollow, sleeve 18 prevents the hollow, compressible infusion sleeve from collapsing against the hollow, vibrating needle.

Figure 2:
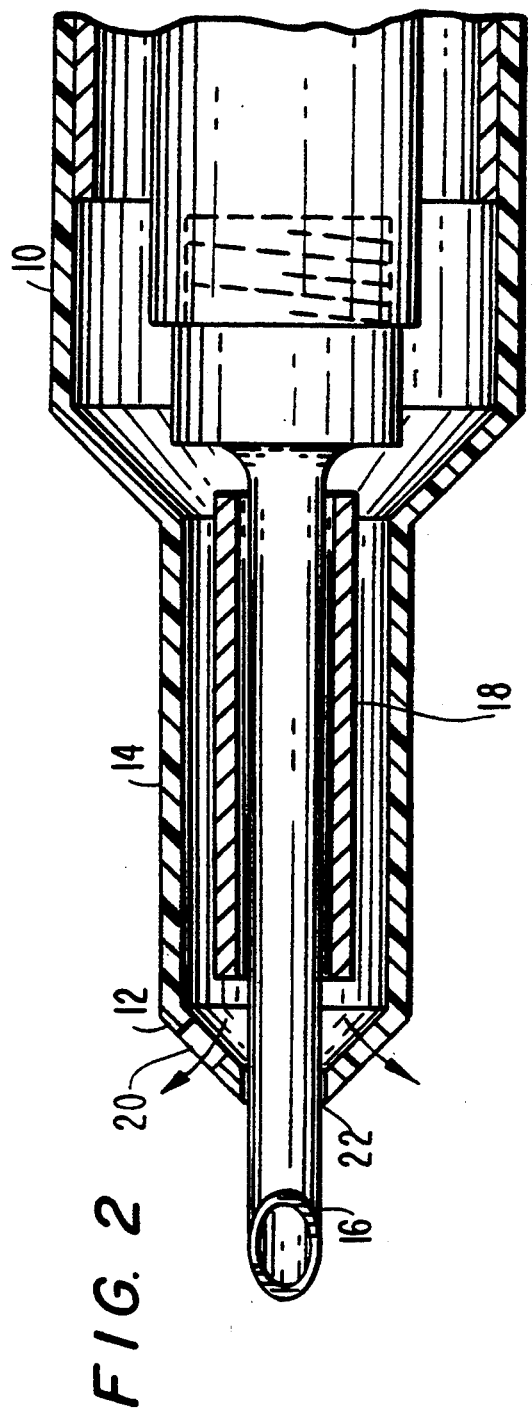
FIG. 2 depicts an embodiment of a phacoemulsification instrument in accordance with the invention; including details of a rigid, hollow sleeve as well as details of the outer deformable sleeve tightly conforming to the vibrating needle at the tapered distal end.

FIG. 2 depicts an embodiment of the invention in which the outer deformable sleeve 10 closely conforms to the vibrating needle at the tapered distal end 12. The close fit between the outer deformable sleeve 10 and the vibrating ;needle limits distal migration of the rigid, hollow sleeve 18.

Figure 3:
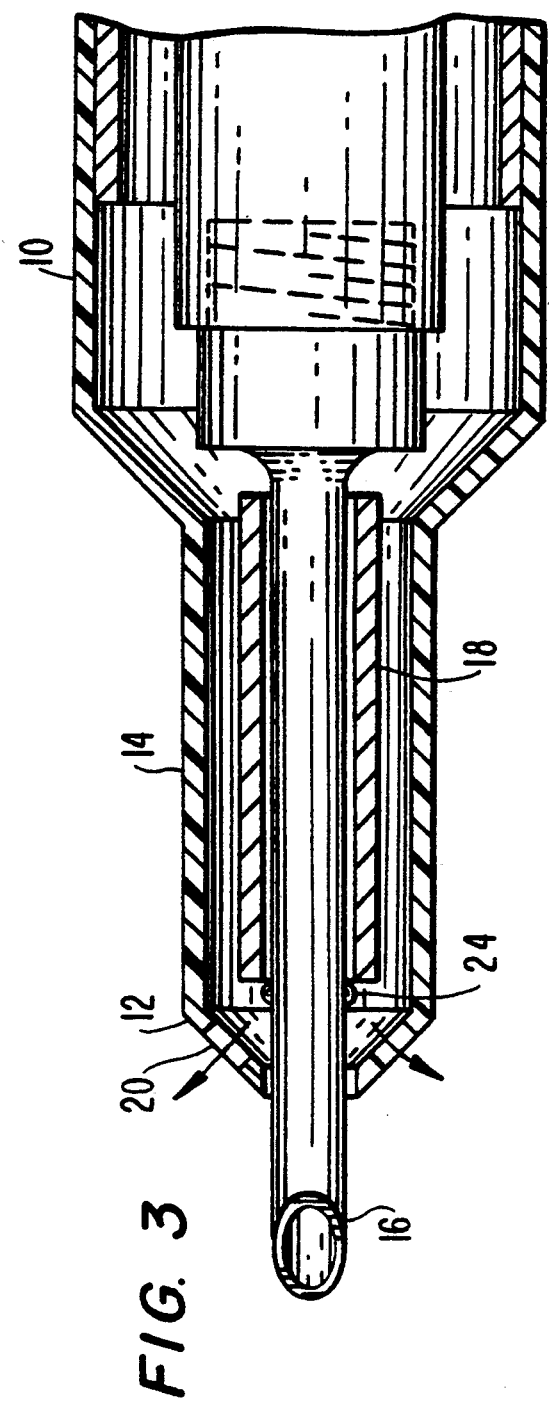
FIG. 3 depicts a second embodiment of a phacoemulsification instrument in accordance with the invention; including details of a rigid, hollow sleeve along with details of a vibrating needle containing protuberances.

FIG. 3 depicts an embodiment of the invention in which the vibrating needle 16 has protuberances 24 at selected points around the periphery thereof. These protuberances 24 limit distal migration of the rigid, hollow sleeve 18.

FIG. 4 depicts an embodiment of the invention wherein the vibrating needle 16 has an inward taper which defines a proximal portion and a distal portion of the needle. The distal portion has a relatively large inner diameter I1—I1 and outer diameter O1—O1. The proximal portion has a smaller inner diameter and outer diameter. As illustrated in FIG. 4, this difference in diameter limits distal migration of the rigid, hollow sleeve 18, since the outer diameter of the distal portion of the needle is larger than the inner diameter of sleeve 18. In the illustrated embodiment, the wall thickness of the needle is substantially constant.

FIG. 5 depicts an embodiment of the invention having a tapered vibrating needle with a distal portion and a proximal portion. The outer diameter of the proximal portion is smaller than the outer diameter of the distal portion, while the inner diameter of the needle remains constant along the length of the needle. Thus, the wall thickness of the proximal portion is reduced. This geometry limits distal migration of sleeve 18, since the outer diameter of the distal portion of the needle is larger than the inner diameter of sleeve 18.

FIG. 6 depicts an embodiment of the invention wherein the rigid hollow sleeve 18 has a ported proximal expansion portion 26 and a threaded extension 28 which is externally and internally threaded. The threaded extension 28 screwably attaches to the needle support 29 which axially oscillates the needle with the threaded extension 28 preventing distal migration of the rigid, hollow sleeve 18. The ports 27 allow saline solution to flow around the rigid, hollow sleeve 18. The figure further shows that the hollow compressible infusion sleeve 10 is screwably attached to external threads of the rigid, hollow sleeve threaded extension.

FIG. 7 depicts an embodiment of the invention wherein the rigid hollow sleeve 18 has a ported proximal flange portion 30. The ported proximal expansion end portion 30 limits distal migration of the rigid hollow sleeve 18 by abutting against an internal shoulder 11 of the hollow compressible infusion sleeve 10. Again, the ports 27 allow saline solution to flow around the rigid, hollow sleeve 18 internal threads on the hollow compressible infusion sleeve 10 mate with external threads needle support 29.

FIG. 8 depicts an embodiment of the invention wherein the rigid hollow sleeve 18 has a ported proximal flange portion 30. The ported proximal flange portion 30 is received in an annular slot in the hollow compressible infusion sleeve 10 and prevents distal migration of the rigid hollow sleeve 18.

FIG. 9 depicts a side view of a rigid, hollow sleeve 18 of a phacoemulsification instrument wherein the rigid, hollow sleeve 18 includes spacers 1 which can be located at each end of the sleeve or its spaced locations along the inner diameter thereof. The spacers 1 prevent large surface contact between the hollow, vibrating needle 16 and the rigid, hollow sleeve 18, while still allowing the maximum amount of fluid to circulate between the rigid, hollow sleeve 18 and the hollow, vibrating needle 16. As will be obvious to one skilled in the art, there is still no need for absolute concentricity, and only a minimal amount of surface area of the rigid, hollow sleeve 18 will come into contact with the hollow, vibrating needle 16.

In the embodiment shown in FIGS. 1–8 the hollow, compressible infusion sleeve 10 may be constructed of silicone or other compressible materials. The rigid, hollow sleeve 18 may be formed of a rigid plastic or other suitable material. Further, discharge ports 20 are angled for radial discharge of fluid thus avoiding the direction of fluid parallel to the needle 16, which would oppose the fractured cataract being drawn into the interior of the hollow vibrating needle 16.

In the embodiment of the invention shown in FIG. 2, as well as in the other embodiments shown, it is noteworthy that the tapered, ported, distal end 12 of the silicone infusion sleeve 10 will not be compressed against the vibrating needle 16 since this portion of the instrument is never maintained within the incision during periods of vibration of the needle 16.

It will thus be seen that the invention efficiently attains the objects set forth above, among those made apparent from the preceding description. In particular, the invention provides a relatively inexpensive, improved apparatus for performing cataract surgery. Those skilled in the art will appreciate that the configurations depicted in FIGS. 1–5 and in FIG. 7 eliminate the previous requirement of concentricity between the hollow, vibrating needle and the rigid, hollow sleeve that was dictated by prior designs. Those skilled in the art will also appreciate that the configurations depicted in FIGS. 6 and 8 further remove the problem of distal migration of the inner sleeve.

It will be understood that changes may be made in the above construction and in the foregoing sequences of operation without departing from the scope of the invention. It is accordingly intended that all matter contained in the above description or shown in the accompanying drawings be interpreted as illustrative rather than in a limiting sense.

It is also to be understood that the following claims are intended to cover all of the generic and specific features of the invention as described herein, and all statements of the scope of the invention which, as a matter of language, might be said to fall therebetween.

Having described the invention, what is claimed as new and secured by Letters Patent is:

1. A surgical instrument for removing a cataract through an incision in a patient's eye, comprising:

a hollow, compressible infusion sleeve;
   said hollow, compressible infusion sleeve having a tapered, ported, distal end portion and having an extreme end portion;
   said hollow, compressible infusion sleeve further including a cylindrical portion;
   said cylindrical portion intersecting with and extending away from said tapered, ported, distal end portion;
   a hollow, vibrating needle, having an inner needle diameter, an outer needle diameter and a wall thickness,
   said hollow, vibrating, needle extending into a patient's eye during the removal of a cataract;
   a needle support;
   said cylindrical portion and said tapered, ported, distal end portion surrounding said hollow, vibrating needle with there being a space between the extreme end portion of said tapered, ported distal end portion and the hollow, vibrating needle;
   a rigid, hollow, sleeve surrounding a portion of said hollow, vibrating needle with said rigid, hollow, sleeve having a sleeve body, an outer sleeve diameter, and an inner sleeve diameter,
   said inner sleeve diameter being larger than said outer needle diameter, thereby defining a path of fluid between said hollow vibrating needle and said rigid, hollow, sleeve;
   said rigid, hollow, sleeve being surrounded by said cylindrical portion whereby said rigid, hollow, sleeve prevents the hollow, compressible infusion sleeve from collapsing against said hollow, vibrating needle; and an inhibitor for inhibiting the distal migration of said rigid, hollow, sleeve.

2. A surgical instrument for removing a cataract through an incision in a patient's eye according to claim 1, wherein said inhibiting means includes:
   a ported proximal flange portion intersecting and extending outward from said sleeve body,
   a threaded extension, said threaded extension intersecting with and extending away from said ported proximal flange portion,
   said threaded extension being screwably engageable with said hollow, vibrating needle, needle support.

3. A surgical instrument for removing a cataract through an incision in a patient's eye according to claim 1, wherein
   said inhibiting means includes a ported proximal flange portion intersecting and extending outward from said sleeve body to limit migration of said rigid hollow sleeve towards said tapered ported distal end.

4. A surgical instrument for removing cataracts through an incision in a patient's eye according to claim 3, wherein
   said hollow compressible infusion sleeve contains a slot for receiving said rigid hollow sleeve; and
   said rigid, hollow sleeve is coupled to said hollow compressible infusion sleeve.

5. A surgical instrument for removing a cataract through an incision in a patient's eye according to claim 1, wherein
   said rigid, hollow sleeve further comprises spacers attached to said sleeve body, said spacers extending inward towards a longitudinal axis of said rigid hollow sleeve.

* * * * *